# (12) United States Patent
Schilt et al.

(10) Patent No.: US 6,834,837 B2
(45) Date of Patent: Dec. 28, 2004

(54) SURGICAL INSTRUMENT SUPPORT DEVICE AND METHOD

(75) Inventors: Janice L. Schilt, Irvine, CA (US); William J. Kotelee, Broadview Heights, OH (US)

(73) Assignee: Rultract, Inc., Cleveland, OH (US)

(*) Notice: Subject to any disclaimer, the term of this patent is extended or adjusted under 35 U.S.C. 154(b) by 0 days.

(21) Appl. No.: 10/289,985

(22) Filed: Nov. 7, 2002

(65) Prior Publication Data

US 2004/0089777 A1 May 13, 2004

(51) Int. Cl.[7] .................................................. E04G 3/00
(52) U.S. Cl. .............................. 248/284.1; 248/276.1; 248/292.13; 600/227; 600/228
(58) Field of Search ...................... 248/280.11, 292.11, 248/276.1, 279.1, 284.1, 292.12, 292.13; 600/227, 228, 229, 231; 128/845

(56) References Cited

U.S. PATENT DOCUMENTS

| | | |
|---|---|---|
| 373,362 A | 11/1887 | Hamilton |
| 1,048,750 A | 12/1912 | Smith |
| 1,242,688 A | 10/1917 | Hawley |
| 1,400,616 A | 12/1921 | McCrory et al. |
| 1,747,799 A | 2/1930 | Straus |
| 1,914,202 A | 6/1933 | Henze et al. |
| 3,403,675 A | 10/1968 | Carr |
| 3,542,015 A | 11/1970 | Steinman |
| 3,643,655 A | 2/1972 | Peronti |
| 3,710,783 A | 1/1973 | Jascalevich |
| 3,823,709 A | 7/1974 | McGuire |

(List continued on next page.)

FOREIGN PATENT DOCUMENTS

SU 1210800 2/1986

OTHER PUBLICATIONS

Transaxillary Approach for First Rib Resection to Relieve Thoracic Outlet Syndrome, David B. Roos, M.D., from the Department of Surgery, University of Colorado School of Medicine, Annals of Surgery, pp. 354–358, Mar. 1966.

(List continued on next page.)

Primary Examiner—Leslie A. Braun
Assistant Examiner—Tan Le
(74) Attorney, Agent, or Firm—Renner, Otto, Boisselle & Sklar, LLP

(57) ABSTRACT

A surgical instrument support device and method for positioning a surgical instrument relative to a surface of a surgical support platform are disclosed. The support device includes a base member, an elongated support member, an extender bar, and a securing mechanism. The base member is fixably mountable to the surgical support platform. The elongated support member has one end mounted to the base member for pivotal movement of the elongated support member relative to the base member within a pivot plane that is nonparallel to the surface of the surgical support platform. The extender bar is adapted for mounting a surgical instrument with respect thereto and is disposed at the other end of the elongated support member. The extender bar projects from the elongated support member such that the pivotal movement of the elongated support member raises or lowers the extender bar and the surgical instrument mounted with respect thereto with respect to the surface of the surgical support platform. The securing mechanism selectively locks and unlocks the elongated support member relative to the base member to respectively prevent and allow the pivotal movement.

32 Claims, 8 Drawing Sheets

U.S. PATENT DOCUMENTS

| | | | |
|---|---|---|---|
| 3,910,538 A * | 10/1975 | Baitella | 248/124.1 |
| 4,099,521 A | 7/1978 | Nestor et al. | |
| 4,143,652 A | 3/1979 | Meier et al. | |
| 4,151,838 A | 5/1979 | Crew | |
| 4,457,300 A | 7/1984 | Budde | |
| 4,461,284 A * | 7/1984 | Fackler | 600/228 |
| 4,473,074 A * | 9/1984 | Vassiliadis | 606/19 |
| 4,622,955 A | 11/1986 | Fakhrai | |
| 4,627,421 A | 12/1986 | Symbas et al. | |
| 4,702,465 A | 10/1987 | McConnell | |
| 4,726,356 A | 2/1988 | Santilli et al. | |
| 4,813,401 A | 3/1989 | Grieshaber | |
| 4,829,985 A | 5/1989 | Couetil | |
| 4,863,133 A * | 9/1989 | Bonnell | 248/280.11 |
| 4,865,019 A | 9/1989 | Phillips | |
| 4,945,897 A | 8/1990 | Greenstein et al. | |
| 4,953,540 A | 9/1990 | Ray et al. | |
| 4,971,038 A | 11/1990 | Farley | |
| 4,995,875 A | 2/1991 | Coes | |
| 5,025,779 A | 6/1991 | Bugge | |
| 5,088,472 A | 2/1992 | Fakhrai | |
| 5,109,831 A | 5/1992 | Forrest et al. | |
| 5,334,194 A | 8/1994 | Mikhail | |
| 5,545,123 A | 8/1996 | Ortiz et al. | |
| 5,551,660 A * | 9/1996 | Leduchowski | 248/276.1 |
| 5,613,939 A | 3/1997 | Failla | |
| 5,616,117 A | 4/1997 | Dinkler et al. | |
| 5,667,481 A | 9/1997 | Villalta et al. | |
| 5,803,903 A | 9/1998 | Athas et al. | |
| 5,876,333 A | 3/1999 | Bigliani et al. | |
| 5,938,592 A | 8/1999 | Koteles et al. | |
| 5,957,135 A | 9/1999 | Molina | |
| 5,964,699 A | 10/1999 | Rullo et al. | |
| 5,984,866 A | 11/1999 | Rullo et al. | |
| 6,083,153 A | 7/2000 | Rullo et al. | |
| 6,090,042 A | 7/2000 | Rullo et al. | |
| 6,209,835 B1 * | 4/2001 | Walrath et al. | 248/276.1 |
| 6,210,324 B1 | 4/2001 | Reno | |
| 6,220,556 B1 * | 4/2001 | Sohrt et al. | 248/279.1 |
| 6,228,026 B1 | 5/2001 | Rullo et al. | |
| 6,354,994 B1 | 3/2002 | Rullo et al. | |
| 6,488,621 B1 | 12/2002 | Rullo et al. | |

OTHER PUBLICATIONS

Thoracic Outlet Syndrome, David B. Roos, M.D. and J. Cuthbert Owens, M.D., Arch Surg., vol. 93, pp. 71–74, Jul. 1966.

KNY Scheerer Corp., Catalog of Surgical Instruments dated 1959, pp. 70–75 and 90–92.

The Surgical Armamentarium, V. Mueller, dated 1973, pp. 68, 281, 346, 347.

The Surgical Armamentarium, American V. Mueller, dated 1980, pp. 74, 75, 78, 87, 88.

Codman & Shurtleff, Inc., Catalog for Surgical Products dated 1984, pp. 431–437.

Stainless Steel Retractors catalog dated Dec. 18, 1939.

* cited by examiner

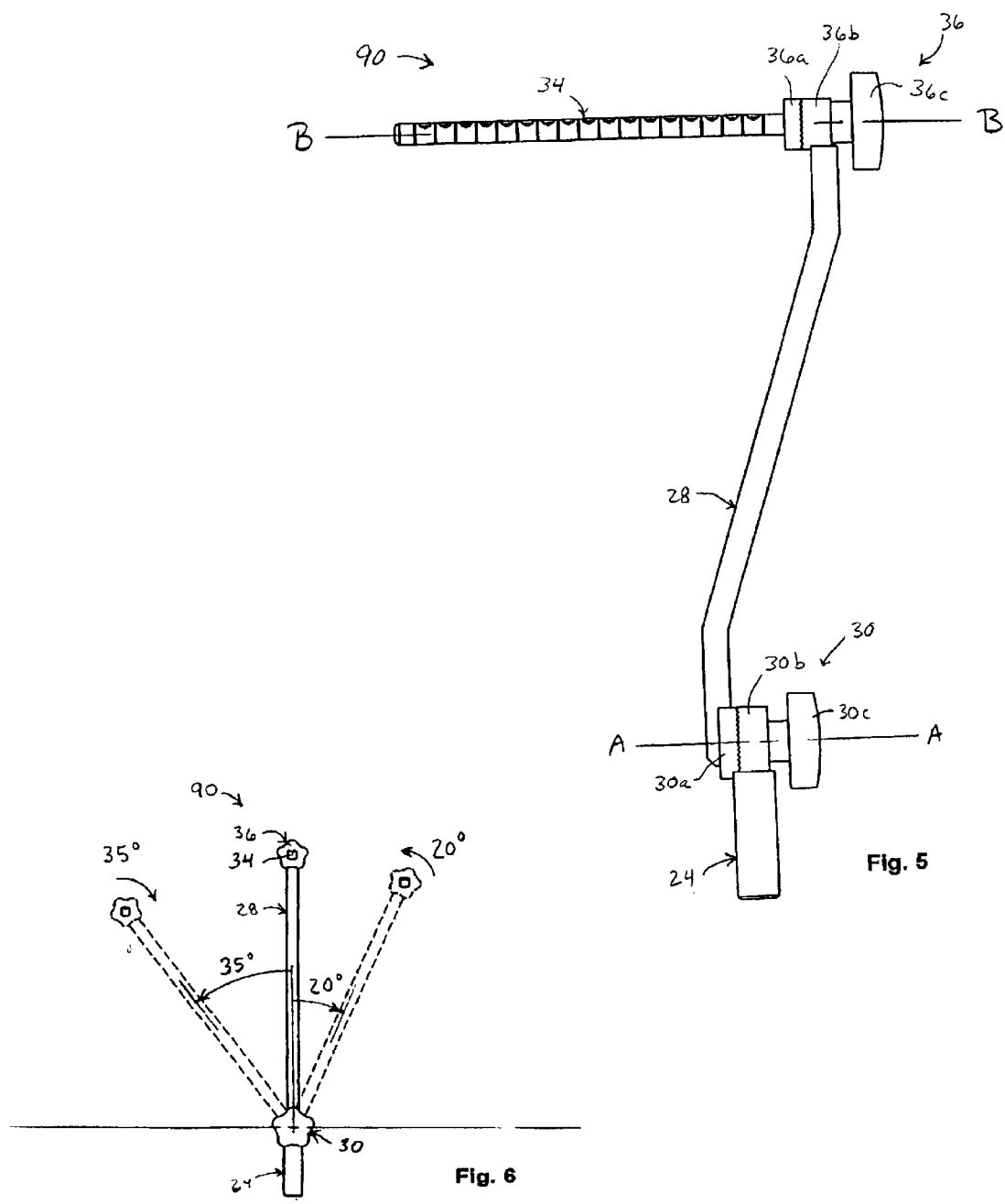

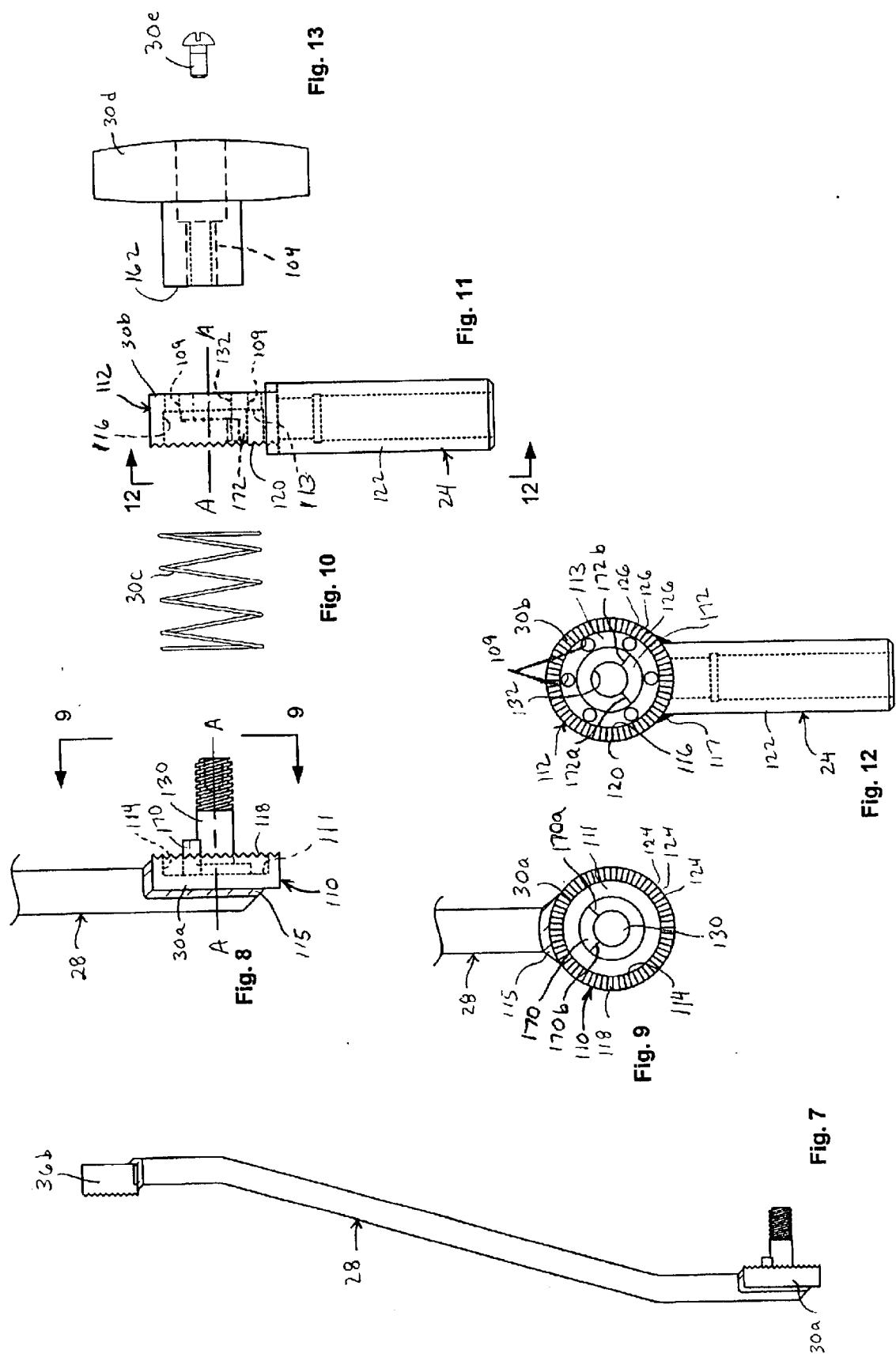

SURGICAL INSTRUMENT SUPPORT DEVICE AND METHOD

TECHNICAL FIELD

The present invention relates generally to a surgical instrument support device and method and, more particularly, to a surgical instrument support device upon which a surgical device, such as a retractor or the like, may be operably mounted.

BACKGROUND OF THE INVENTION

Surgical support apparatuses are used to hold and/or position a surgical instrument in such a manner as to provide a surgeon a clear opening to a patient during surgical procedures. Various improvements have been made to these apparatuses to simplify implementation and positioning of surgical instruments, while keeping the surgeon's hands free, so that the surgeon, assistant or other user need not break off performing an act in order, for example, to displace the surgical instrument.

However, most of the various known surgical support devices afford limited flexibility in their positioning or repositioning, or the positioning or repositioning of the surgical instrument supported by the surgical support device. For example, some prior art support devices have a combination of support members that are adjustable only in a linear motion. Oftentimes, such devices require a combination of a number of linear movements of the various support members before a desired position of the support device and surgical instrument may be obtained in which the surgeon's range of action is unobstructed. What is needed is a surgical support apparatus which provides a wide range of possible positions for placement of surgical devices, such as retractors.

SUMMARY OF THE INVENTION

The present invention provides a surgical instrument support device that can be easily adjusted to a wide variety of desired positions without obstructing the surgeon's range of action.

According to one aspect of the invention, a surgical instrument support device for positioning a surgical instrument relative to a surface of a surgical support platform, includes a base member, an elongated support member, an extender bar, and a securing mechanism. The base member is fixably mountable to a surgical support platform. The elongated support member has one end mounted to the base member for pivotal movement of the elongated support member relative to the base member within a pivot plane that is nonparallel to the surface of the surgical support platform. The extender bar is adapted for mounting a surgical instrument with respect thereto, and is disposed at the other end of the elongated support member and projects from the elongated support member such that the pivotal movement of the elongated support member raises or lowers the extender bar and the surgical instrument mounted with respect thereto with respect to the surface of the surgical support platform. The securing mechanism selectively locks and unlocks the elongated support member relative to the base member to respectively prevent and allow pivotal movement.

According to another aspect of the invention, there is provided a method of supporting a surgical instrument relative to a patient positioned relative to a surface of a surgical support platform. The method includes the steps of providing an elongated support member having one end mounted to a base member for pivotal movement of the elongated support member relative to the base member within a pivot plane that is nonparallel to the surface of the surgical support platform, and an extender bar at the other end of the elongated support member, the extender bar projecting from the elongated support member, mounting a surgical instrument with respect to the extender bar, pivoting the elongated support member, thereby to raise or lower the extender bar with respect to the surface of the surgical support platform, and, using a securing mechanism to lock and prevent pivotal movement of the elongated support member relative to the base member.

According to another aspect of the invention, a surgical instrument support device for positioning a surgical instrument extender bar relative to a surface of a surgical support platform, includes an elongated support member, an extender bar, and a securing mechanism. The elongated support member is fixably mountable with respect to the surface of the surgical support platform. The extender bar is mounted to the elongated support member for swivelling movement of the extender bar relative to the elongated support member above the surface of the surgical support platform. The securing mechanism selectively locks and unlocks the extender bar relative to the elongated support member to respectively prevent and allow swivelable movement.

According to still another aspect of the invention, there is provided a method of supporting a surgical instrument relative to a patient positioned relative to a surface of a surgical support platform. The method includes the steps of providing an elongated support member disposed with respect to the surface of the surgical support platform, and an extender bar mounted to the elongated support member for swivelling movement of the extender bar relative to the elongated support member above the surface of the surgical support platform, mounting a surgical instrument with respect to the extender bar, swiveling the extender bar to position the extender bar with respect to the surface of the surgical support platform, and, using a securing mechanism to lock and prevent swivelable movement of the extender bar relative to the elongated support member.

According to an aspect of the invention, an extension device for a surgical instrument support device having a support bar includes a clamp portion, an extender bar portion, and a securing mechanism. At least one receptacle is disposed in the clamp portion for receiving the support bar from the surgical instrument support device, the clamp portion being positioned to retain the support bar in the receptacle. The extender bar portion is mounted to the clamp portion for pivotal movement of the extender bar portion relative to the clamp portion. The securing mechanism selectively locks and unlocks the extender bar portion relative to the clamp portion to respectively prevent and allow pivotal movement.

According to another aspect of the invention, there is provided a method of supporting a surgical instrument relative to a patient positioned relative to a surface of a surgical support platform. The method includes the steps of providing a first extender bar disposed above the surface of the surgical support platform, mounting an extension device with respect to the first extender bar, the extension device including a clamp portion, a second extender bar, and a securing mechanism, the second extender bar being mounted to the clamp portion for pivotal movement relative to the clamp portion, the securing mechanism being operative to selectively lock and unlock the second extender bar relative to the clamp portion to respectively prevent and allow pivotal movement, mounting a surgical instrument with respect to the second extender bar, pivoting the second extender bar relative to the clamp portion to position the second extender bar with respect to the surface of the surgical support platform, and, using the securing mechanism to lock and prevent pivotal movement of the second extender bar relative to the clamp portion.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 5 is a front elevational view of a surgical instrument support device in accordance with the present invention.

FIG. 6 is a schematic side elevational view of the surgical instrument support device of FIG. 5, the support device being shown in a vertical orientation in solid lines, and angularly displaced from the vertical orientation in dashed lines.

FIG. 7 shows an elongated support member of the surgical instrument support device of FIG. 5, and part of a securing mechanism disposed at a pivot end thereof.

FIG. 8 is an enlarged view of the pivot end of the FIG. 7 elongated support member, showing the part of the securing mechanism in greater detail.

FIG. 9 is a side view of the pivot end of the FIG. 7 elongated support member, as seen from the line 9—9 in FIG. 8, showing the part of the securing mechanism in greater detail.

FIG. 10 shows a spring of the surgical instrument support device of FIG. 5.

FIG. 11 shows a base member of the surgical instrument support device of FIG. 5, and part of a securing mechanism disposed at a pivot end thereof.

FIG. 12 is a side view of the FIG. 11 base member, as seen from the line 12—12 in FIG. 11, showing the part of the securing mechanism in greater detail.

FIG. 13 shows a knob and stop of the securing mechanism of the surgical instrument support device of FIG. 5.

DETAILED DESCRIPTION OF THE INVENTION

Figure 1:
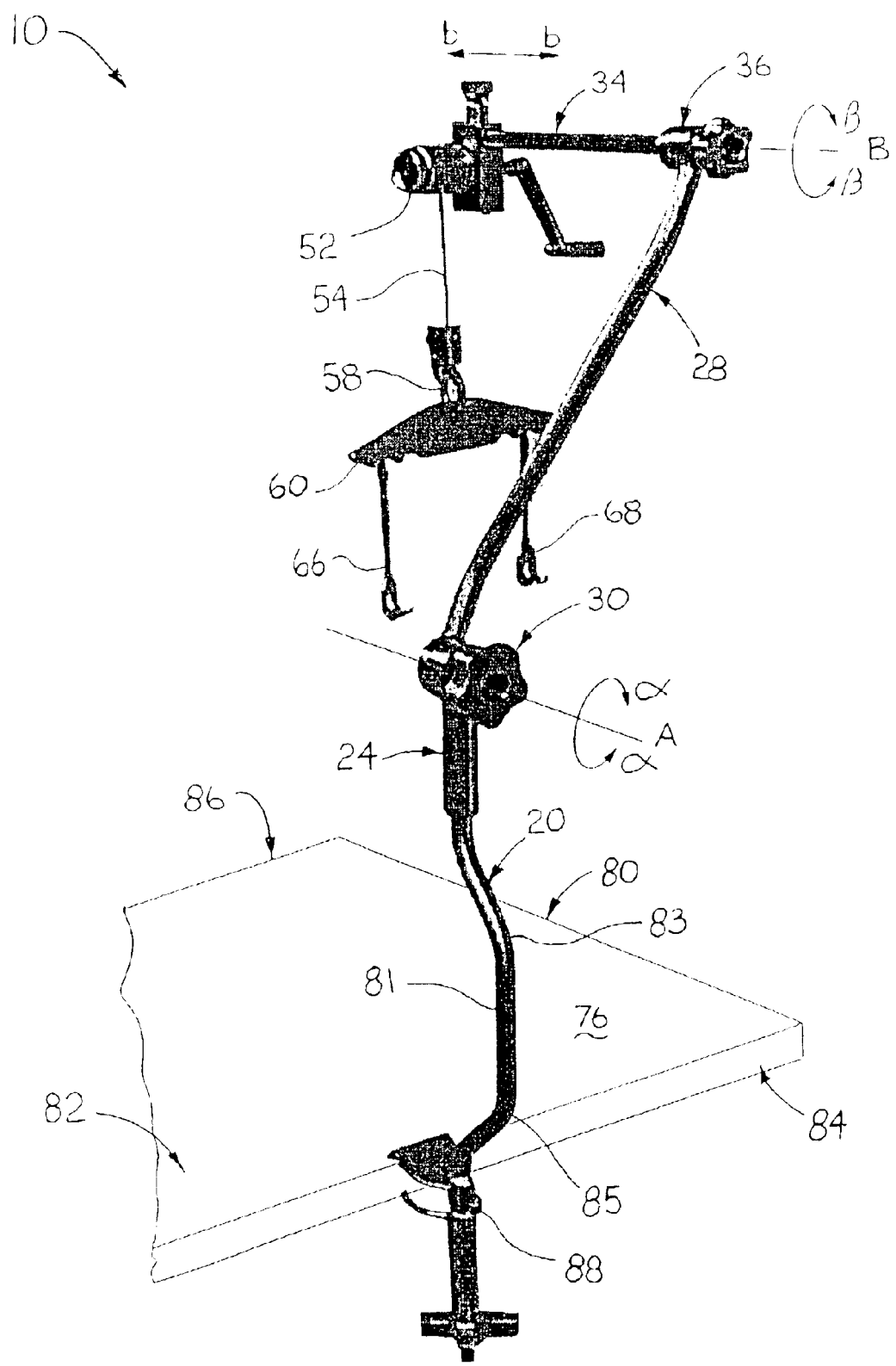
FIG. 1 is a perspective view of an embodiment of a surgical instrument support system in accordance with the present invention, the support system being shown supporting a lifting device, rake plate and pair of rakes.
Figure 2:
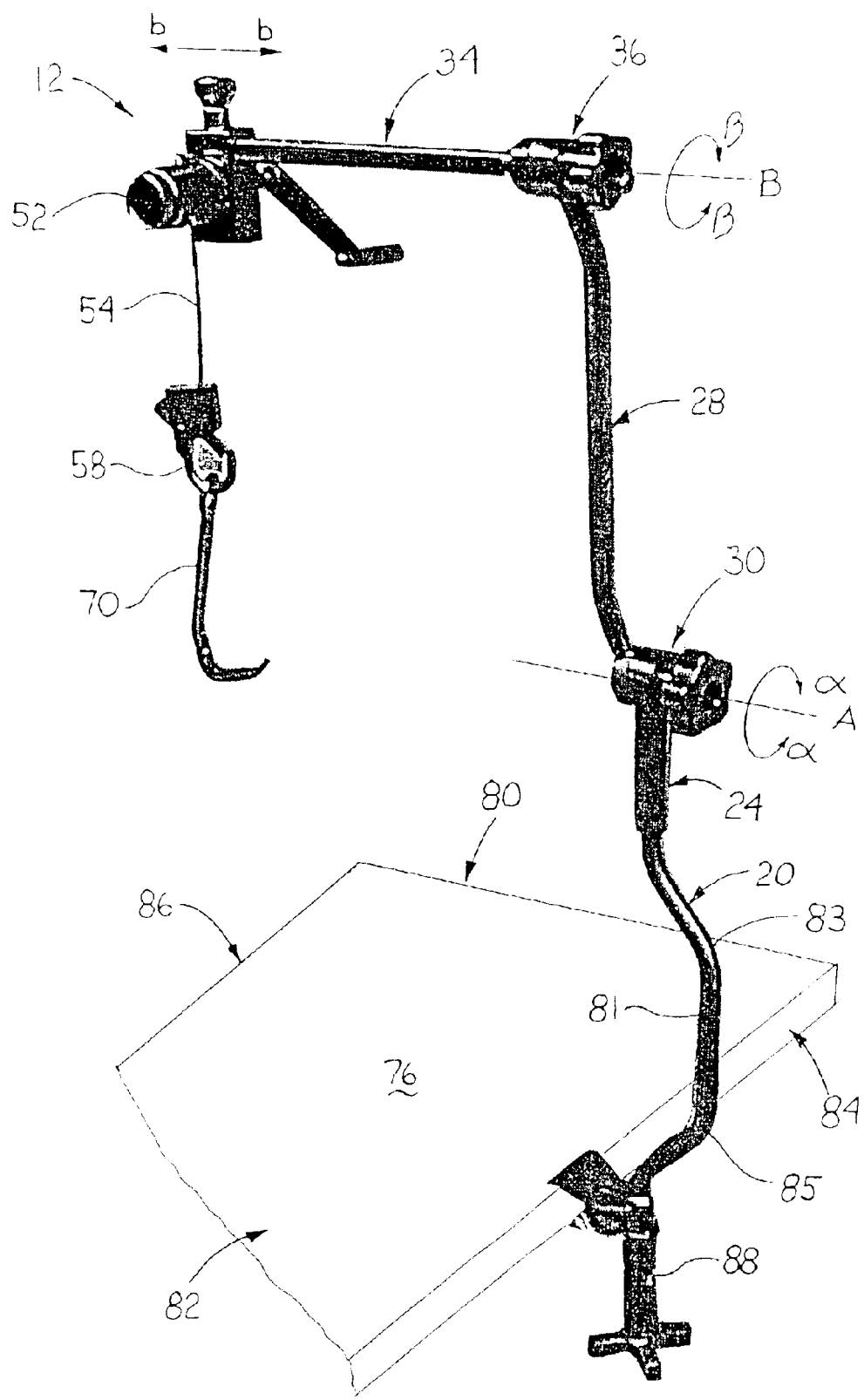
FIG. 2 is a perspective view of an embodiment of a surgical instrument support system in accordance with the present invention, the support system being shown supporting a lifting device and a rake.

In the detailed description which follows, where considered appropriate, reference numerals have been repeated among the figures to indicate corresponding elements, regardless of whether they are shown in different embodiments of the present invention. To illustrate the present invention in a clear and concise manner, the drawings may not necessarily be to scale and certain features may be shown in somewhat schematic form. For example, the dimensions of some of the elements are exaggerated relative to each other for clarity.

to FIGS. 1–4, FIGS. 1–4, there are shown four exemplary embodiments of a surgical instrument support system in accordance with the present invention generally indicated at, respectively, reference numerals 10, 12, 14 and 16, each of which is mounted to a surgical surgical support platform 18, such as an operating table. The surgical instrument support systems 10, 12, 14 and 16 each include a riser member 20, a base member 24, an elongated support member 28, a first securing mechanism 30 for locking the elongated support member 28 to the base member 24, an extender bar 34, a second securing mechanism 36 for securing the extender bar 34 to the elongated support member 28, and a surgical instrument. The illustrated extender bar 34 has a rectilinear cross section, and in one embodiment a square cross section.

Figure 3:
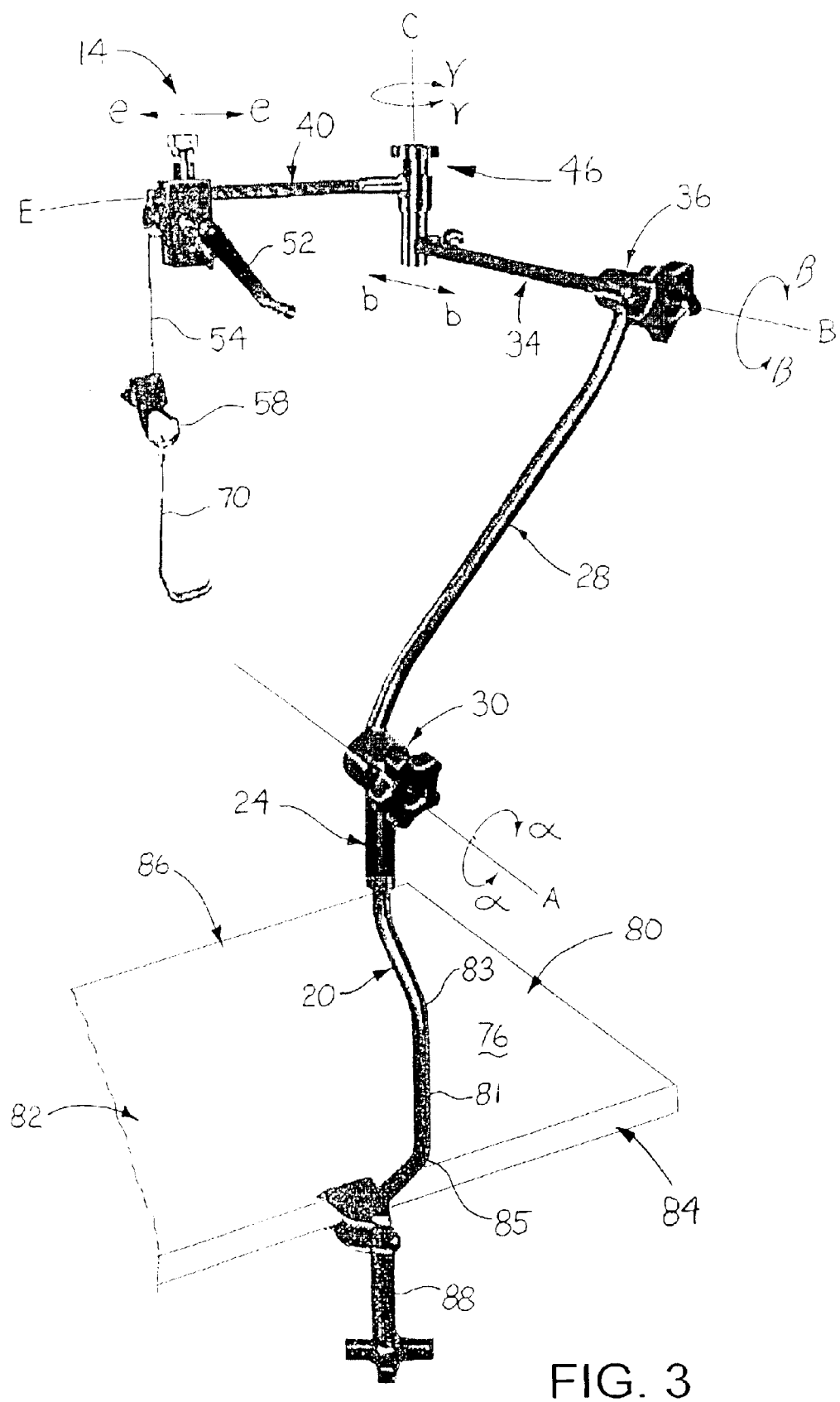
FIG. 3 is a perspective view of an embodiment of a surgical instrument support system in accordance with the present invention, the support system being shown supporting a lifting device and a rake.
Figure 4:
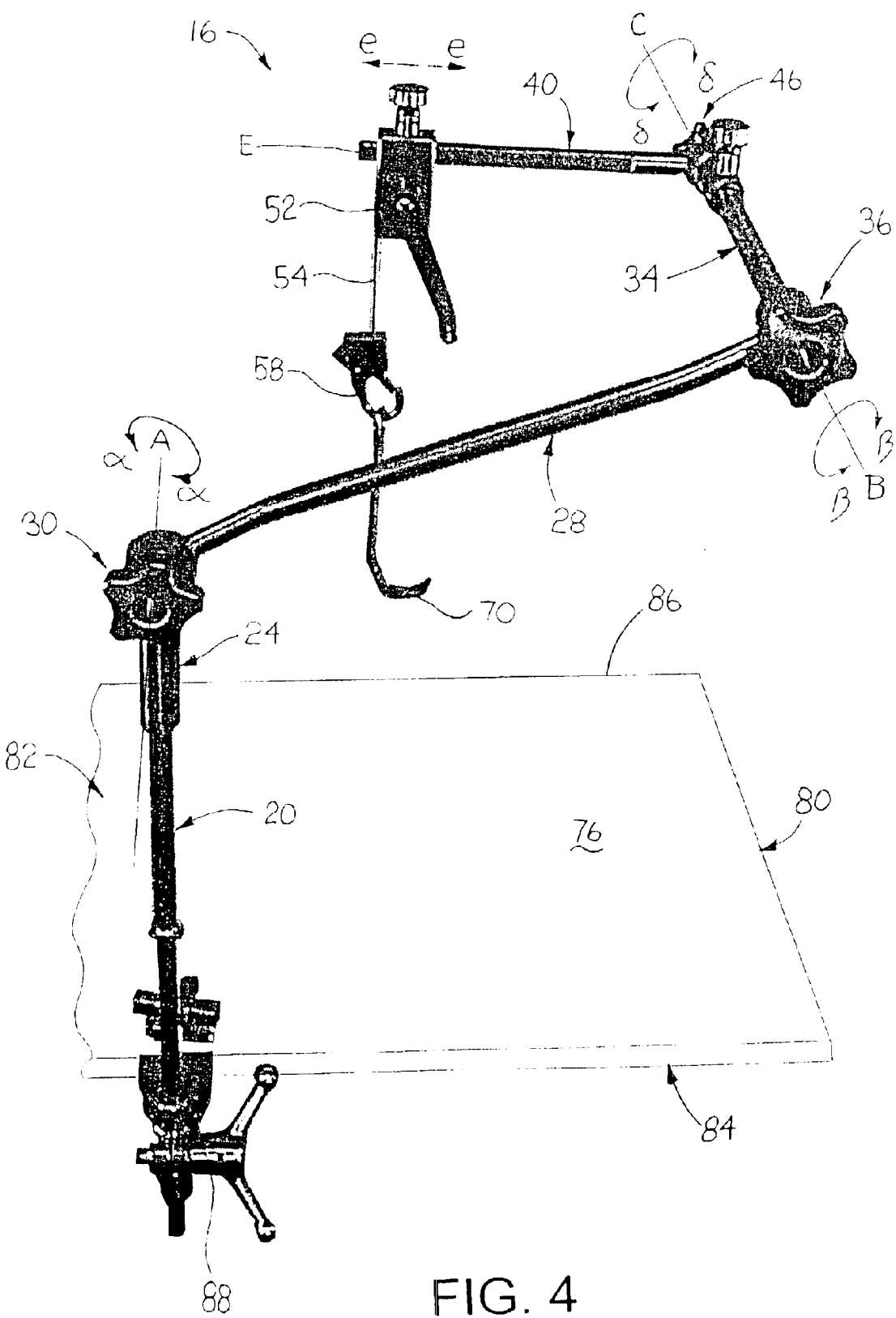
FIG. 4 is a perspective view of an embodiment of a surgical instrument support system in accordance with the present invention, the support system being shown supporting a lifting device and a rake.

The support systems 14 and 16 illustrated in FIGS. 3 and 4 further include an extension device 40 mounted to the extender bar 34. The extension device 40 includes an extender bar portion 42, which in one embodiment in cross section geometry is substantially the same as that of the extender bar 34, and a clamp portion 44 which allows the extension device 40 to be secured to the extender bar 34 in a plurality of orientations, two of which are shown, respectively, in FIGS. 3 and 4. A third securing mechanism 46 secures the extender bar portion 42 to the clamp portion 44.

In accordance with the invention, the particular structure and arrangement of the components forming the exemplary surgical instrument support systems 10, 12, 14 and 16 enable the surgical instrument to be raised or lowered, moved transversely from right to left or vice versa, moved longitudinally from head to toe or vice versa, and/or be angularly displaced in a variety of planes to achieve a wide range of surgical instrument positions. The flexibility in positioning and/or repositioning of the surgical instrument and the surgical instrument support systems 10, 12, 14 and 16, and the ease with which the support systems 10, 12, 14 and 16 may be accessed and adjusted, simplify implementation and positioning of a surgical instrument relative to a patient on the surgical support platform 18. These and other advantages, as well as the structure, function and features of the surgical instrument support systems 10, 12, 14 and 16 are described in greater detail below.

The surgical instrument of the illustrated support systems 10, 12, 14 and 16 includes a ratcheting lifting device 52, a cable 54, and a snap clip 58. The surgical instrument shown in FIG. 1 further includes a rake plate 60 and a pair of rakes 66 and 68, and the surgical instrument shown in FIGS. 2, 3 and 4 further includes a rake 70. The rake plate 60, or rake 70, may be raised or lowered via the cable 54, which is connected to the lifting device 52. Further details of these and other exemplary surgical instruments which may be used with the present invention may be had by reference to U.S. Pat. Nos. 6,387,047; 6,354,994; 6,228,026; 6,083,153; 5,984,866; 5,964,699; 5,957,135; and 5,938,592, all of which are assigned to the assignee of the present invention and are hereby incorporated herein by reference in their entireties, for their teachings relating to such devices.

Each surgical instrument support system 10, 12, 14 and 16 is mounted to the surgical support platform 18. Of course, the surgical instrument support system 10, 12, 14 and 16 may alternatively be mounted to the surgery room floor or other suitable mounting surface, so long as the surgical instrument support system 10, 12, 14 and 16 is fixed relative to the surgical support platform 18. Also, it will be appreciated that the surgical instrument support system 10, 12, 14 and 16 need not include the riser member 20, for example in surgical operations in which the surgical instrument may be disposed relatively lower than that illustrated, in which case the base member 24 may be mounted to the surgical support platform 18 or other mounting surface.

In the illustrated embodiments, the surgical support platform 18 is generally rectangular in shape, having a head end 80 (the right end in FIGS. 1–4), a toe end 82 (the left end in FIGS. 1–4), and right and left sides 84 and 86, respectively. The riser member 20 of each surgical instrument support system 10, 12, 14 and 16 is releasably attachable to the surgical support platform 18 by a suitable attachment clamp 88. Although the illustrated riser member 20 is mounted to the right side 84 of the surgical support platform 18, the riser member 20 may alternatively be attached to the head end 80, the toe end 82, or to the left side 86 of the surgical support platform 18, as will be appreciated. In the illustrated embodiments, the riser member 20 extends generally perpendicularly with respect to the right side 84 and top surface of the surgical support platform 18. As will be appreciated, the riser member 20 may extend at an angle other than 90 degrees relative to the right side 84 and/or top surface of the surgical support platform 18. For example, it may be desirable that the riser member 20 project inwardly towards the center of the surgical support platform 18. In another embodiment, the riser member 20 may depend from the ceiling or from a wall of a surgery room.

As is shown in FIGS. 1–4, the illustrated riser member 20 includes an outwardly extending portion 81 including the bends 83 and 85. The outwardly extending portion 81 is above the level of the surgical support platform 18 so as to provide additional space in the surgical field around the patient. In an alternative embodiment, the riser member 20 does not include an outwardly extending portion, so that there are no bends. Further details of other riser members may be found in, for example, the aforementioned U.S. Pat. Nos. 6,387,047 and 6,228,026.

The base member 24 is mounted to the upper portion of the riser member 20. The elongated support member 28, in turn, is mounted to the base member 24 for pivotable movement about a pivot axis A, the arc α—α being representative of such pivoting motion of the elongated support member 28. The extender bar 34 is mounted to the upper or distal end of the elongated support member 28 for swivellable movement about a swivel axis B, the arc β—β being representative of such swivelling movement of the extender bar 34. In the support systems 10 and 12, the surgical instrument, and more particularly the ratcheting lifting device 52 thereof, is slidable axially with respect to the extender bar 34 along the axis B, the arrows b—b being representative of the motion of the surgical instrument. In the support system 14, the extension device 40 is slidable axially with respect to the extender bar 34 along the axis B, and the extender bar portion 42 thereof is pivotable about an axis C, which in the FIG. 3 orientation is substantially perpendicular to the axis B. The arrows b—b in FIG. 3 are representative of the motion of the extension device 40 and the arc γ—γ is representative of the pivoting motion of the extender bar portion 42. In the support system 16, the extension device 40 is mounted to the distal end of the extender bar 34, and the extender bar portion 42 thereof is pivotable about the axis C, which in the FIG. 4 orientation is substantially collinear with the axis B. The arc δ—δ in FIG. 4 is representative of the pivoting motion of the extender bar portion 42. The ratcheting lifting device 52 in the support systems 14 and 16 is slidable axially with respect to the extender bar portion 42 along the axis E, the arrows e—e being representative of the motion of the surgical instrument.

Turning to FIG. 5, an embodiment of the base member 24, the first securing mechanism 30, the elongated support member 28, the second securing mechanism 36, and the extender bar 34, which together form a single surgical instrument support device 90, is illustrated. The support device 90 may form part of a surgical instrument support system, such as the support systems 10, 12, 14 and 16 of FIGS. 1–4, or be incorporated as a modular device into an existing surgical instrument support system.

The FIG. 5 support device 90 provides angular displacement capabilities in both the elongated support member 28 and the extender bar 34. Thus, the elongated support member 28 is pivotable relative to the base member 24 about the pivot axis A, and the extender bar 34 is swivellable relative to the upper or distal end of the elongated support member 28 about the swivel axis B. In an alternative embodiment, the base member 24 and elongated support member 28 may be constructed as a single device, for example, with an extender bar that is integral with and non-swivelling relative to the elongated support member 28. In another alternative embodiment, the extender bar 34 and elongated support member 28 may be constructed as a single device, for example, with the elongated support member 28 being integral with and non-pivoting relative to the base member 24. All such alternative embodiments are contemplated by and fall within the purview of the claimed invention.

In the illustrated embodiment, the extender bar 34 projects perpendicularly from the elongated support member 28. In this way, pivoting the elongated support member 28 relative to the base member 24 raises or lowers the extender bar 34 relative to the horizontal while also maintaining the extender bar 34 parallel relative to the horizontal. As will be appreciated, the extender bar 34 may project from the elongated support member 28 at any non-parallel angle to effect raising or lowering of the extender bar 34 with pivoting of the elongated support member 28.

The extender bar 34 may be swivelled or angularly displaced substantially the same amount as the elongated support member 28 is pivoted relative to the base member 24 to maintain the extender bar 34, and the surgical instrument supported thereby, in the same orientation as before such angular displacement. For example, in the right portion of FIG. 6, the elongated support member 28 is shown tilted clockwise, for example towards the head end 80 of the surgical support platform 18 in FIGS. 1–4, about 20 degrees from vertical, and the extender bar 34 is shown swivelled counterclockwise about 20 degrees. In the left portion of FIG. 6, the elongated support member 28 is shown tilted counterclockwise, for example towards the toe end 82 of the surgical support platform 18 in FIGS. 1–4, about 35 degrees from vertical, and the extender bar 34 is shown swivelled clockwise about 35 degrees. For either angular displacement, the top and bottom surfaces of the extender bar 34 are maintained parallel with respect to the horizontal. Thus, in this embodiment a surgical instrument, such as the ratcheting lifting device 52 illustrated in FIGS. 1–4, mounted to the extender bar 34 has a different vertical elevation but the same horizontal orientation after angular displacement as it does before angular displacement.

In an embodiment, the extender bar 34 may swivel automatically, for example as by gravitational force exerted by the surgical instrument, as the elongated support member 28 is tilted. Alternatively, the swivelling of the extender bar 34 and the pivoting of the elongated support member 28 may require two separate actions on the part of the user.

In each of the support systems 10, 12, 14 and 16 illustrated in FIGS. 1–4, the elongated support member 28 pivots within a plane that is substantially perpendicular to the top surface of the surgical support platform 18. It will be appreciated that such pivot plane may be at any suitable non-parallel angle with respect to the surgical support platform 18. This may be accomplished, for example, by mounting the riser member 20 to the surgical support platform 18 so that the riser member 20 projects at a non-parallel angle relative to the top surface of the surgical support platform 18. Alternatively, this may be accomplished by adapting the pivot connection of the base member 24 and the elongated support member 28 such that the elongated support member 28 pivots in a plane that is at a non-parallel angle relative to the top surface of the surgical support platform 18.

The support device 90 (FIG. 6) includes two securing mechanisms 30 and 36 (FIGS. 1–4) disposed, respectively, at the junction or pivot end of the elongated support member 28 (FIG. 7) and the base member 24 (FIG. 11), and at the junction or swivel end of the extender bar 34 (FIG. 14) and the elongated support member 28. The securing mechanism 30 allows a user to lock or unlock the elongated support member 28 relative to the base member 24. In a similar manner, the securing mechanism 36 allows a user to lock or unlock the extender bar 34 relative to the elongated support member 28.

Details of an exemplary securing mechanism 30 and an exemplary means of pivotably mounting the elongated support member 28 to the base member 24 are shown in FIGS. 7–13. FIG. 7 shows the elongated support member 28, and FIGS. 8 and 9 show in greater detail an embodiment of the proximal end 30a of the elongated support member 28, which proximal end 30a is pivotably mounted to the base member 24. FIGS. 11 and 12 show in greater detail an embodiment of the base member 24. FIGS. 10 and 13 show, respectively, a spring 30c and a knob 30d, which also form part of the illustrated securing mechanism 30.

The securing mechanism 30 includes a pair of engaging members 110 and 112. In one embodiment, the male engaging member 110 is disposed at the proximal or lower end 30a of the elongated support member 28. In one embodiment, the female engaging member 112 is disposed at the distal or upper end 30b of the base member 24. In other embodiments, the respective engaging members 110 and 112 may be reversed from the positions shown in FIG. 7. For example, in one embodiment the male engaging member 110 may be disposed at the distal or upper end 30b of the base member 24, and the female engaging member 112 may be disposed at the proximal or lower end 30a of the elongated support member 28.

Each engaging member 110 and 112 is somewhat U-shape in cross section. The U-shape is defined by a bottom wall 111 and 113 and a cylindrical wall 114 and 116 projecting from the respective bottom wall 111 and 113. In the illustrated embodiment, the bottom wall 113 of the female engaging member 112 includes six holes or apertures 109 (FIGS. 11 and 12) circumferentially disposed on a common radius relative to the axis A. The apertures 109 extend through the thickness of the bottom wall 113 and provide ventilation to the interior of the female engaging member 112. Also, the apertures 190 provide convenient access to the U-shape cavity to enable cleaning of same.

As is shown in FIGS. 7–9, the male engaging member 110 and the proximal end 30a of the elongated support member 28 are attached together such that the elongated bar portion of the elongated support member 28 projects radially from the axis A of the male engaging member 110. In one embodiment, as illustrated, the bottom wall 111 and an arcuate portion of the cylindrical wall 114 are welded by a weld 115 to an inverted L-shape corner machined into the elongated bar portion. As is shown in FIGS. 11 and 12, the female engaging member 112 and a cylindrical coupling portion 122 of the base member 24 are attached together such that the cylindrical coupling portion 122 projects radially from the axis A of the female engaging member 112. In one embodiment, as illustrated, an arcuate portion of the cylindrical wall 116 is welded by a weld 122 (FIG. 12) to an arcuate shape recess machined into the cylindrical coupling portion 122. In one embodiment, the welds are smooth and continuous and free of seams, cracks, pinholes or other openings into which contaminants could become lodged. These members may be suitably attached by other known methods, for example by casting or forging as a single piece.

The projecting ends of the cylindrical walls 114 and 116 form respective engaging surfaces 118 and 120. In the illustrated embodiment, the engaging surfaces 118 and 120 include a plurality of circumferentially disposed teeth 124 and 126 (FIGS. 9 and 12) that are disposed on a common radius relative to the axis A. The teeth 124 are able to mesh with and engage the opposing teeth 126 to lock the engaging members 110 and 112. The number of teeth 124 selected is based on the angular displacement capability desired for a particular surgical instrument support system. The exemplary engaging members 110 and 112 of FIGS. 9 and 12 include 60 teeth 124 and 126 equally circumferentially spaced apart six (6) degrees. In this manner, the elongated support member 28 may be adjusted to engage the base member 24 in six degree increments, providing a total of 60 different angular positions.

The male engaging member 110 includes a pivot shaft 130. The pivot shaft 130 is slidably received in a through hole 132 of the female engaging member 112, enabling the female engaging member 112 to be pivoted about the pivot shaft 130. The pivot shaft 130 has a longitudinal axis A, which is the same as the aforementioned pivot axis A in the support systems 10, 12, 14 and 16 illustrated in FIGS. 1–4. The elongated support member 28, and more particularly the male engaging member 110 thereof, is relatively axially slidable with respect to the base member 24, and more particularly the female engaging member 112 thereof, along the axis A via the mating connection between the pivot shaft 130 and the through hole 132. By axially sliding the engaging members 110 and 112 towards one another, the toothed surfaces 118 and 120 of the engaging members 110 and 112 may be brought into engagement, thereby engaging the elongated support member 28 and base member 24 and preventing relative pivotal movement therebetween. By axially sliding the engaging members 110 and 112 away from one another, the toothed surfaces 118 and 120 of the engaging members 110 and 112 may be relatively disengaged, allowing the elongated support member 28 to be pivoted relative to the base member 24 about the pivot axis A.

In the illustrated exemplary embodiment, the elongated support member 28 and base member 24 are spring biased axially apart by means of a spring 30c (FIG. 10) sandwiched between the engaging members 110 and 112 of the securing mechanism 30. The opposite ends of the spring 30c are captured in the U-shape cavities formed by the cylindrical shape walls 114 and 116 and the bottom walls 111 and 113 of the respective engaging members 110 and 112. 2a The opposite ends of the spring 30c are seated on the bottom walls 111 and 113. The spring 30c biases the engaging members 110 and 112 away from one another, that is, into relative axial disengagement. When the engaging members 110 and 112 are sufficiently urged apart so that a gap exists between the planes of the crowns of the teeth 124 and 126 of the respective toothed surfaces 118 and 120, the engaging members 110 and 112 may be pivoted relative to one another.

The securing mechanism 30 includes a knob 30d (FIG. 13) that includes a threaded portion 104 that threadingly engages the shaft 130. The threaded portion 104 of the knob 30d is operative to force the engaging members 110 and 112, and therefore the elongated support member 28 and the base member 24, into relative engagement and to lock same into position, or to allow relative disengagement of the engaging members 110 and 112. To urge the engaging members 110 and 112 into engagement, the knob 30d is first rotated towards the base member 24 until an end wall 162 of the knob 30d abuts the backside of the bottom wall 113 of the female engaging member 112. The knob 30d is then further rotated to urge the female engaging member 112 axially along the shaft 130, thereby axially sliding the engaging members 110 and 112 into engagement and locking same together. The toothed surfaces 118 and 120 of the engaging members 110 and 112 self-align relative to one another and guide the elongated support member 28 into engagement with the base member 24 into one of the aforementioned 60 different angular positions. Although not illustrated, the end wall 162 may be equipped with a bronze bushing or other suitable bearing member to provide for smooth engagement between the end wall 162 and the backside of the bottom wall 113 of the female engaging member 112. To unlock and disengage the engaging members 110 and 112, the knob 30d need merely be axially backed away from the male engaging member 110 and the spring 30c will urge the female engaging member 112 axially along the shaft 130 and away from the male engaging member 110.

In the illustrated embodiment, the securing mechanism 30 also includes a stop such as a screw 30e (FIG. 13) that is threaded into the end of the shaft 130. The stop 30e limits the distance that the knob 30d may be axially displaced from the male engaging member 110 of the elongated support member 28. In this embodiment, when the knob 30d reaches such a limit the engaging members 110 and 112 are sufficiently spaced apart so that a gap exists between the planes of the crowns of the teeth 124 and 126 of the respective toothed surfaces 118 and 120 so as to enable the engaging members 110 and 112, and accordingly the elongated support member 28 and the base member 28, to be pivoted relative to one another.

Referring to FIGS. 9 and 12, in the illustrated embodiment the securing mechanism 30 includes arcuate shape cams 170 and 172 which limit the range of relative angular displacement between the engaging members 110 and 112 and, consequently, the elongated support member 28 and the base member 24. In the illustrated embodiment, the cams 170 and 172 are on a common radius with respect to the axis A (FIGS. 8 and 11), and each cam 170 and 172 has about a 90 degree arcuate span on said radius. As viewed in FIG. 9, the cam 170 is disposed in the upper portion of the male engaging member 110 and, as viewed in FIG. 12, the cam 172 is disposed in the lower portion of the female engaging member 112. The cams 170 and 172 contact one another to prevent further relative rotation between the engaging members 110 and 112 beyond a predetermined angular displacement. For example, the edge 170a of the cam 170 abuts the edge 172a of the cam 172 when the elongated support member 28 is tilted towards the head end 80 of the surgical support platform 18 (FIGS. 1–4 and 6) sufficiently to bring the respective edges 170a and 172a together. The edge 170b of the cam 170 abuts the edge 172b of the cam 172 when the elongated support member 28 is tilted towards the toe end 82 of the surgical support platform 18. In another embodiment, the cams 170 and 172 may be omitted.

In the illustrated embodiment, the cams 170 and 172 limit the range of relative pivotal movement between the elongated support member 28 and the base member 24 to about 90 degrees from vertical in either the clockwise or counterclockwise direction. As will be appreciated, in this embodiment the extender bar 34 likewise has a limited range within which it may be raised or lowered, corresponding substantially to the angular displacement limit of the elongated support member 28, since the vertical displacement of the extender bar 34 is a function of the angular displacement of the elongated support member 28. As will further be appreciated, the cams 170 and 172 may be sized and dimensioned to obtain other suitable angular displacement limits, or may be omitted altogether.

Referring again to the stop 30e of the securing mechanism 30, the stop 30e limits the axial distance that the knob 30d can be axially displaced or backed away from the male engaging member 110. This ensures that the cams 170 and 172 contact one another when the elongated support member 28 and the base member 24 are pivoted relative to one another. In an alternative embodiment, the stop 30e may be adapted to allow the knob 30d to be backed away from the male engaging member 110 so as to provide a rotational clearance between the cams 170 and 172. Such clearance may be suitable, for example, when it is desired to enable a wider range of relative pivotal movement of the elongated support member 28 and the base member 24 than that which is provided by the cams 170 and 172.

It will be appreciated that the illustrated exemplary securing mechanism 30 is but one way of enabling selective locking and unlocking of the elongated support member 28 relative to the base member 24 to respectively prevent and allow relative pivotal movement between the elongated support member 28 and the base member 24. Means other than the illustrated toothed surfaces 118 and 120 may be used to provide engagement between the engaging members 110 and 112. For example, the engaging members 110 and 112 may be equipped with a relatively high friction material such as rubber, or sintered metal. Additionally, or alternatively, a C-clamp or similar device may be used to lock or unlock the elongated support member 28 relative to the base member 24.

Referring now to FIGS. 14–18, details of the securing mechanism 36 and an exemplary means of swivellably mounting the extender bar 34 to the elongated support member 28 will now be described. Except as described herein, the securing mechanism 36 is substantially the same as the afore described securing mechanism 30.

Figure 14:
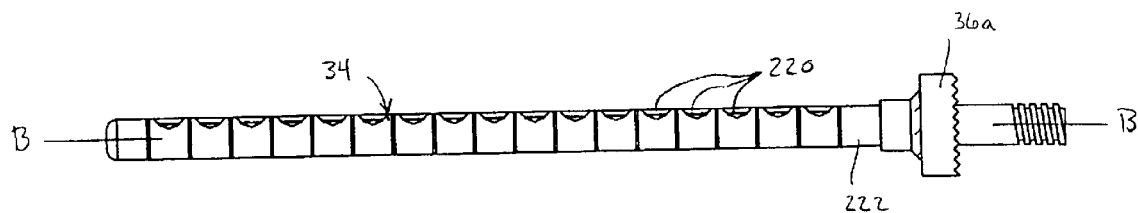
FIG. 14 shows an extender bar of the surgical instrument support device of FIG. 5, and part of a securing mechanism disposed at a swivel end thereof.
Figure 15:
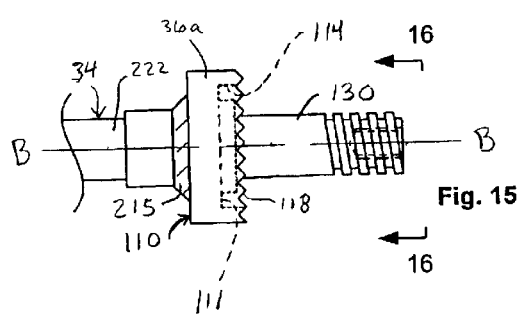
FIG. 15 is an enlarged view of the swivel end of the FIG. 14 extender bar, showing the part of the securing mechanism in greater detail.
Figure 17:
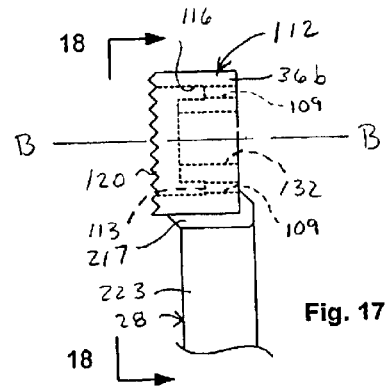
FIG. 17 is an enlarged view of a swivel end of the FIG. 7 elongated support member, and part of a securing mechanism disposed at the swivel end.
Figure 16:
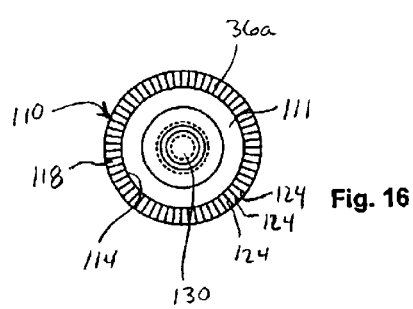
FIG. 16 is a side view of the swivel end of the FIG. 14 extender bar, as seen from the line 16—16 in FIG. 15, showing the part of the securing mechanism in greater detail.
Figure 18:
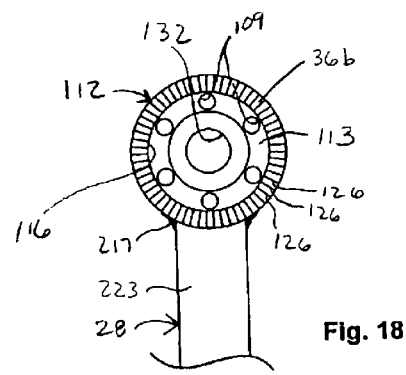
FIG. 18 is a side view of the swivel end of the FIG. 7 elongated support member and part of the securing mechanism, as seen from the line 18—18 in FIG. 17.
Figure 19:
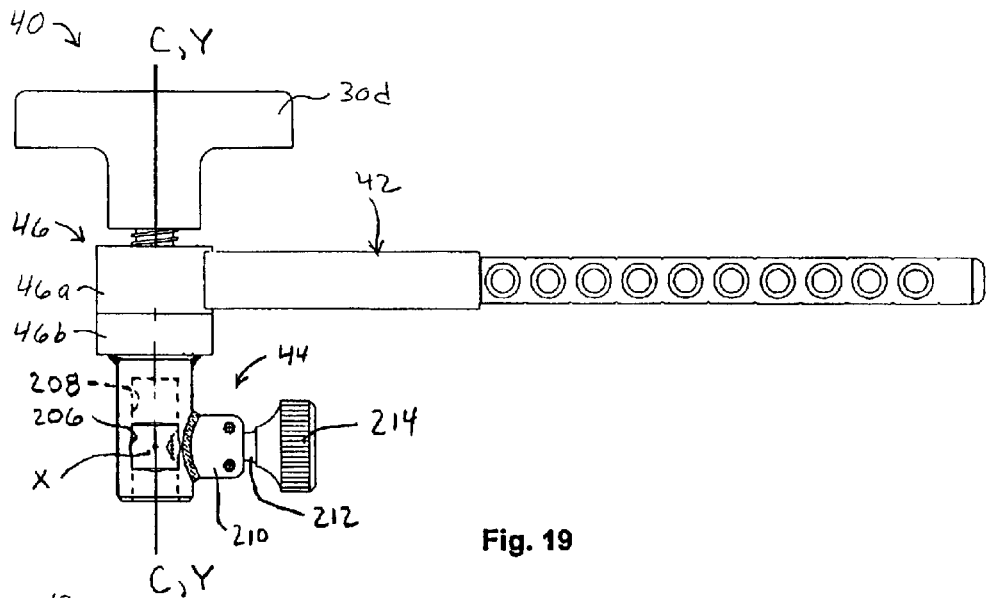
FIG. 19 is a front elevational view of an extension device in accordance with the present invention for a surgical instrument support device having a support bar.

FIG. 14 shows the extender bar 34, and FIGS. 15 and 16 show in greater detail an embodiment of the proximal end 36a of the extender bar 34, which proximal end 36a is swivelably mounted to the distal or upper end 36b of the elongated support member 28 (FIG. 7). FIGS. 17 and 18 show an embodiment of the distal end 36b of the elongated support member 28 in greater detail. The securing mechanism 36 includes a spring 30c, a knob 30d, and a stop 30e (FIGS. 10 and 13), although these components are not shown in the illustrated securing mechanism 36.

Like the securing mechanism 30, the securing mechanism 36 includes a pair of engaging members 110 and 112, except that in the illustrated embodiment the male engaging member 110 is disposed at the proximal end 36a of the extender bar 34, and the female engaging member 112 is disposed at the distal or upper end 36b of the elongated support member 28. In other embodiments, the respective engaging members 110 and 112 may be reversed from the positions shown in FIGS. 7 and 14. For example, in one embodiment the male engaging member 110 may be disposed at the distal or upper end 36b of the elongated support member 28, and the female engaging member 112 may be disposed at the proximal end 36a of the extender bar 34. In such case, a yoke connection may be desirable whereby, for example, the proximal end 36a of the extender bar 34 takes the form of a two prong fork, the prongs being axially spaced along the axis B, that is suitably configured to slidably receive the male engaging member 110 in a radial direction with respect to the axis B such that the centerline of the shaft 130 of the male engaging member 130 aligns collinearly with the axis B. Also, to facilitate such radial movement, the female engaging member 112 may include a radially projecting slot sized to radially receive the shaft 130 of the male engaging member 110.

In the illustrated embodiment, the bottom wall 113 of the female engaging member 112 includes six holes or apertures 109 (FIGS. 17 and 18) circumferentially disposed on a common radius relative to the axis B. The apertures 109 extend through the thickness of the bottom wall 113 and provide ventilation to the interior of the female engaging member 112. Also, the apertures 190 provide convenient access to the U-shape cavity to enable cleaning of same.

As is shown in FIG. 15, the male engaging member 110 and the proximal end 36a of the extender bar 34 are attached together such that the elongated bar portion 222 of the extender bar 34 is coincidentally aligned with respect to the male engaging member 110 along the axis B, which is the same as the aforementioned swivel axis B in the support systems 10, 12, 14 and 16 illustrated in FIGS. 1–4. In one embodiment, the bottom wall 111 of the male engaging member 110 is welded by a weld 215 to the elongated bar portion 222. As is shown in FIGS. 17 and 18, the female engaging member 112 and an elongated bar portion 223 of the elongated support member 28 are attached together such that the elongated bar portion 222 projects radially from the axis B of the female engaging member 112. In one embodiment, an arcuate portion of the cylindrical wall 116 is welded by a weld 217 to an arcuate shape recess machined into the elongated bar portion 223. In one embodiment, as illustrated, the welds are smooth and continuous and free of seams, cracks, pinholes or other openings into which contaminants could become lodged. These members may be suitably attached by other known methods, for example by casting or forging as a single piece.

The securing mechanism 36 functions in a manner similar to that described above for the securing mechanism 30. Likewise, the manner by which the extender bar 34 swivels relative to the elongated support member 28 is substantially the same as the manner by which the elongated support member 28 pivots relative to the base member 24. Thus, the extender bar 34 may be locked relative to the elongated support member 28 to prevent relative swivelable movement therebetween by axially sliding the engaging members 110 and 112 towards one another along the axis B such that the toothed surfaces 118 and 120 of the engaging members 110 and 112 engage one another. To enable the extender bar 34 to be swivelled relative to the elongated support member 28 about the swivel axis B, the engaging members 110 and 112 are axially slid away from one another along the axis B such that a gap exists between the planes of the crowns of the teeth 124 and 126 of the respective toothed surfaces 118 and 120.

The threaded portion 104 of the knob 30d is operative to draw the engaging members 110 and 112 together, and thereby force together and relatively lock the extender bar 34 and the elongated support member 28. The spring 30c biases the engaging members 110 and 112 into relative disengagement to allow the extender bar 34 to be swivelled relative to the elongated support member 28. The stop 30e limits the distance that the knob 30d may be axially displaced from the male engaging member 110, which distance is sufficient to provide a gap between the planes of the crowns of the teeth 124 and 126 of the respective toothed surfaces 118 and 120.

Unlike the illustrated embodiment of the securing mechanism 30, the illustrated embodiment of securing mechanism 36 does not include cams that limit the angular displacement between the engaging members 110 and 112. Thus, in this embodiment, the extender bar 34, when unlocked from the elongated support member 28, is free to swivel about the axis B any angular amount. In another embodiment, the cams 170 and 172 are included to provide for limited angular displacement between the extender bar 34 and the elongated support member 28.

It will be appreciated that the illustrated exemplary securing mechanism 36 is but one way of enabling selective locking and unlocking of the extender bar 34 relative to the elongated support member 28 to respectively prevent and allow relative swivellable movement between the extender bar 34 and the elongated support member 28. As with the securing mechanism 30, means other than the illustrated toothed surfaces 118 and 120 may be used to provide engagement between the engaging members 110 and 112 of the securing mechanism 36. For example, the engaging members 110 and 112 may be equipped with a relatively high friction material such as rubber, or sintered metal. Additionally, or alternatively, a C-clamp or similar device may be used to lock or unlock the extender bar 34 and the elongated support member 28.

Referring now to FIGS. 19–23, details of the extension device 40 will now be described. The extension device 40 may form part of a surgical instrument support system, such as shown in the support systems 14 and 16 of FIGS. 3 and 4 in which the extension device 40 is mounted to the extender bar 34, or be incorporated as a modular device into an existing surgical instrument support system, such as those shown and described in the afore-referenced U.S. Pat. Nos. 6,387,047; 6,354,994; 6,228,026; 6,083,153; 5,984,866; 5,964,699; 5,957,135; and 5,938,592.

The extension device 40 includes an extender bar portion 42, a clamp portion 44 and a securing mechanism 46. The extender bar portion 42 is mounted to the clamp portion 44 for pivotal movement of the extender bar portion 42 about the pivot axis C, which is the same as the aforementioned pivot axis C in the support systems 14 and 16 illustrated in FIGS. 3 and 4. The clamp portion 44 allows the extension device 40 to be slid to and fro with respect to the extender bar 34 along the axis B (FIGS. 3-5 and 14), and is operative to secure the extension device 40 to the extender bar 34 in a manner more fully described below. The securing mechanism 46, described in greater detail below, selectively locks and unlocks the extender bar portion 42 relative to the clamp portion 44 to respectively prevent and allow pivotal movement of the extender bar portion 42 about the pivot axis C.

Figure 22:
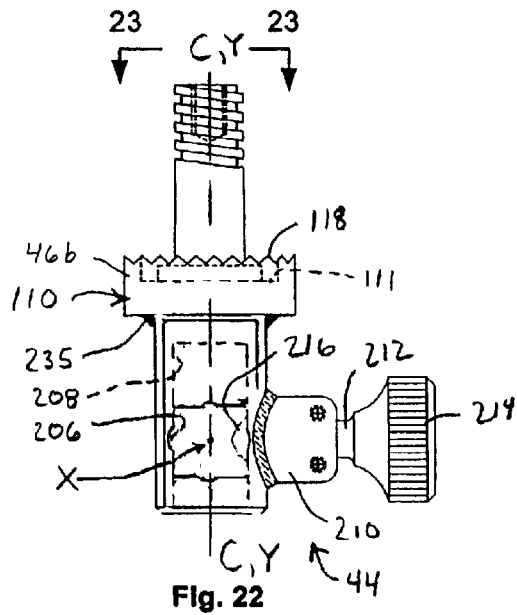
FIG. 22 is an enlarged view of a clamp portion of the extension device of FIG. 19, and part of a securing mechanism disposed at a pivot end of the clamp portion.

The clamp portion 44 includes first and second receptacles 206 and 208 having first and second axes X and Y defining the direction in which the extender bar 34 is received. In the illustrated embodiment, the first axis X is disposed perpendicular to the pivot axis C, the second axis Y is disposed collinearly with the pivot axis C, and the first and second axes X and Y are disposed perpendicular to one another (FIG. 22). The X axis is perpendicular to the plane of the page in FIGS. 19 and 22, and is shown as a period or bullet point. In the illustrated embodiment, the second receptacle 208 is a closed-end opening and, accordingly, the extender bar 34 can be inserted only a relatively short distance into the second receptacle 208. In the illustrated embodiment, the first receptacle 206 is an opening which passes completely through the clamp 204 and, accordingly, the extender bar 34 can be inserted any desired distance into the first receptacle 206.

The receptacles 206 and 208 of the clamp portion 44 enable the extension device 40 to be mounted to the extender bar 34 in a plurality of orientations, two of which are shown for example in FIGS. 3 and 4, respectively. In the orientation in which the extension device 40 is mounted to the extender bar 34 in the surgical instrument support system 14 of FIG. 3, the extender bar portion 42 pivots in a plane that is parallel to the top surface of the surgical support platform 18. In the orientation in which the extension device 40 is mounted to the extender bar 34 in the surgical instrument support system 16 of FIG. 4, the extender bar portion 42 pivots in a plane that is perpendicular to the top surface of the surgical support platform 18. It will be appreciated that the extension device 40 may be mounted to the extender bar 34 in orientations other than those illustrated in FIGS. 3 and 4. For example, because the illustrated extender bar 34 is square in cross section, as is the first receptacle 206, the extension device 40 may be mounted to the extender bar 34 in four different angular positions, each position being spaced 90 degrees apart from its adjacent position. Accordingly, the extension device 40 may be mounted on the extender bar 34 in a position 90 degrees from the orientation shown in the FIG. 3 surgical instrument support device 14, in which case the extender bar portion 42 of the extension device 40 pivots in a plane that is perpendicular to the top surface of the surgical support platform 18.

The clamp portion 204 includes a clamp body 210, a threaded shaft 212 in one embodiment, and a handle 214. In one embodiment, the lower end (opposite the handle) of the shaft 212 is configured to securely fit into a positioning bore such as the bores 220 shown in FIG. 14. The clamp 204 is positioned to retain the extender bar 34 in either the first receptacle 206 or the second receptacle 208. A shaft tip 216 on the threaded shaft 212 interacts with the bores 220 to retain the extender bar 34 in the clamp 204. Further details of the clamp portion 204 and the connection to an extender bar such as the illustrated extended bar 34 may be found in, for example, the aforementioned U.S. Pat. Nos. 6,387,047; 6,228,026; and 5,984,866.

Details of the securing mechanism 46 and an exemplary means of pivotally mounting the extender bar portion 42 to the clamp portion 44 will now be described. Except as described herein, the securing mechanism 46 is substantially the same as the afore described securing mechanisms 30 and 36.

Figure 20:
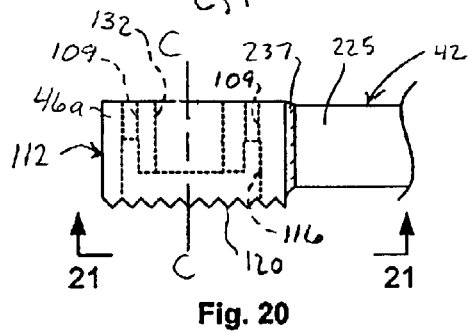
FIG. 20 is an enlarged view of a pivot end of an extender bar portion of the extension device of FIG. 19 and part of a securing mechanism disposed at the pivot end.
Figure 21:
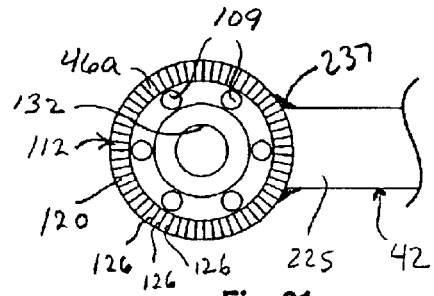
FIG. 21 is a bottom view of the pivot end of the FIG. 20 extender bar portion and part of the securing mechanism, as seen from the line 21—21 in FIG. 20.
Figure 23:
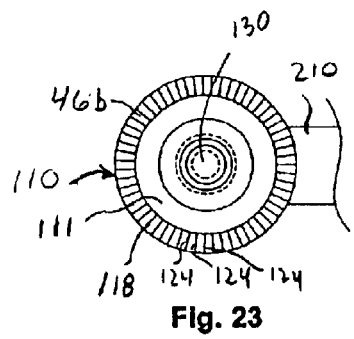
FIG. 23 is a side view of the pivot end of the FIG. 22 clamp portion, as seen from the line 23—23 in FIG. 22.

FIGS. 20 and 21 show in greater detail an embodiment of the proximal end 46a of the extender bar portion 42, which proximal end 46a is pivotally mounted to the distal or upper end 46b of the clamp portion 44. FIGS. 22 and 23 show an embodiment of the distal end 46b of the clamp portion 44 in greater detail. The securing mechanism 46 also includes a knob 30d shown in FIG. 19, a spring 30c and a stop 30e (FIGS. 10 and 13), the spring 30c and stop 30e not being shown in the illustrated securing mechanism 46.

Like the securing mechanisms 30 and 36, the securing mechanism 46 includes a pair of engaging members 110 and 112, except that in the illustrated embodiment the male engaging member 110 is disposed at the distal end 46b of the clamp portion 44, and the female engaging member 112 is disposed at the proximal end 46a of the extender bar portion 42. In other embodiments, the respective engaging members 110 and 112 may be reversed from the positions shown in FIG. 19. For example, in one embodiment the male engaging member 110 may be disposed at the proximal end 46a of the extender bar portion 42, and the female engaging member 112 may be disposed at the distal end 46b of the clamp portion 44. In such case, a yoke connection may be desirable whereby, for example, the distal end 46b of the clamp portion 44 takes the form of a two prong fork, the prongs being axially spaced along the axis C, that is suitably configured to slidably receive the male engaging member 110 in a radial direction with respect to the axis C such that the centerline of the shaft 130 of the male engaging member 130 aligns collinearly with the axis C. Also, to facilitate such radial movement, the female engaging member 112 may include a radially projecting slot sized to radially receive the shaft 130 of the male engaging member 110.

In the illustrated embodiment, the bottom wall 113 of the female engaging member 112 includes six holes or apertures 109 (FIGS. 20 and 21) circumferentially disposed on a common radius relative to the axis C. The apertures 109 extend through the thickness of the bottom wall 113 and provide ventilation to the interior of the female engaging member 112. Also, the apertures 190 provide convenient access to the U-shape cavity to enable cleaning of same.

As is shown in FIGS. 20 and 21, the female engaging member 112 and the proximal end 46a of the extender bar portion 42 are attached together such that the elongated bar portion 225 projects radially from the axis C of the female engaging member 112. In one embodiment, an arcuate portion of the cylindrical wall 116 is welded by a weld 237 to an arcuate shape recess machined into the elongated bar portion 225. As is shown in FIG. 22, the male engaging member 110 and the distal end 46b of the clamp portion 44 are attached together such that the distal end 46b is coincidentally aligned with respect to the male engaging member 110 along the axis C. In one embodiment, the bottom wall 111 of the male engaging member 110 is welded by a weld 235 (FIG. 22) to the distal end 46b. In one embodiment, as illustrated, the welds are smooth and continuous and free of seams, cracks, pinholes or other openings into which contaminants could become lodged. These members may be suitably attached by other known methods, for example by casting or forging as a single piece.

The securing mechanism 46 functions in a manner similar to that described above for the securing mechanisms 30 and 36. Likewise, the manner by which the extender bar portion 42 pivots relative to the clamp portion 44 is substantially the same as the pivoting and swivelling functions of the securing mechanisms 30 and 36. Thus, the extender bar portion 42 may be locked relative to the clamp portion 44 to prevent relative pivoting movement therebetween by axially sliding the engaging members 110 and 112 towards one another along the axis C such that the toothed surfaces 118 and 120 of the engaging members 110 and 112 engage one another. To enable the extender bar portion 42 to be pivoted relative to the clamp portion 44 about the pivot axis C, the engaging members 110 and 112 are axially slid away from one another along the axis C such that a gap exists between the planes of the crowns of the teeth 124 and 126 of the respective toothed surfaces 118 and 120.

The threaded portion 104 of the knob 30d is operative to draw the engaging members 110 and 112 together, and thereby force together and relatively lock the extender bar portion 42 and the clamp portion 44. The spring 30c biases the engaging members 110 and 112 into relative disengagement to allow the extender bar portion 42 to be pivoted relative to the clamp portion 44. The stop 30e limits the distance that the knob 30d may be axially displaced from the male engaging member 110, which distance is sufficient to provide a gap between the planes of the crowns of the teeth 124 and 126 of the respective toothed surfaces 118 and 120.

Unlike the illustrated embodiment of the securing mechanism 30, the illustrated embodiment of the securing mechanism 46 does not include cams that limit the angular displacement between the engaging members 110 and 112. Thus, in this embodiment the extender bar portion 42, when unlocked from the clamp portion 44, is free to pivot about the axis C any angular amount. In another embodiment, the cams 170 and 172 are included to provide for limited angular displacement between the extender bar portion 42 and the clamp portion 44.

It will be appreciated that the illustrated exemplary securing mechanism 46 is but one way of enabling selective locking and unlocking of the extender bar portion 42 relative to the clamp portion 44 to respectively prevent and allow relative pivotal movement between the extender bar portion 42 and the clamp portion 44. As with the securing mechanisms 30 and 36, means other than the illustrated toothed surfaces 118 and 120 may be used to provide engagement between the engaging members 110 and 112 of the securing mechanism 46. For example, the engaging members 110 and 112 may be equipped with a relatively high friction material such as rubber, or sintered metal. Additionally, or alternatively, a C-clamp or similar device may be used to lock or unlock the extender bar portion 42 and the clamp portion 44.

As will be appreciated, in one embodiment, the illustrated securing mechanisms 30, 36 and 46 are compact and, when locked, substantially smooth and continuous and free of seams, cracks, pinholes or other openings into which contaminants could become lodged.

In each of the above described embodiments, the surgical instrument is a ratcheting lifting device 52. It will be appreciated that the surgical instrument may take any form as desired for a particular surgical operation. Also, additional and/or alternative surgical instruments may be supported by the surgical instrument support systems 10, 12, 14 and 16, such as, for example, cardiovascular and thoracic instruments, clamps, diagnostic instruments, ear and eye instruments, mouth and throat instruments, orthopedic instruments, probes and directors, retractors, suture instruments, urological instruments, etc. Also, the extender bar 34 and the extender bar portion 42 each have a rectilinear transverse cross-section for mating with the illustrated ratcheting lifting device 52 and/or extension device 40. It will be appreciated that the cross-section may have any suitable size or geometry to facilitate mounting of a surgical instrument with respect to the extender bar 34 and/or the extender bar portion 42. Similarly, the receptacles of the ratcheting lifting device and/or extension device also may have any suitable size or geometry to receive the extender bar and/or the extender bar portion 42.

Although the invention has been shown and described with respect to several embodiments, it is obvious that equivalents and modifications will occur to others skilled in the art upon the reading and understanding of the specification. The present invention includes all such equivalents and modifications, and is limited only by the scope of the following claims.

What is claimed is:

1. A surgical instrument support device for positioning a surgical instrument relative to a surface of a surgical support platform, the support device comprising:

a base member fixably mountable to a surgical support platform;

an elongated support member having one end mounted to the base member for pivotal movement of the elongated support member relative to the base member within a pivot plane that is nonparallel to the surface of the surgical support platform;

an extender bar adapted for mounting a surgical instrument with respect thereto, the extender bar being disposed at the other end of the elongated support member, the extender bar projecting from the elongated support member at an angle that is nonparallel to the pivot plane of the elongated support member such that the pivotal movement of the elongated support member raises or lowers the extender bar and the surgical instrument mounted with respect thereto with respect to the surface of the surgical support platforms; and a securing mechanism for selectively locking and unlocking the elongated support member relative to the base member to respectively prevent and allow said pivotal movement;

wherein the securing mechanism includes first and second engaging members disposed at the pivot ends of the respective elongated support member and base member, the second engaging member facing and being engageable by the first engaging member, and wherein the securing mechanism is operative to force into relative engagement or to allow relative disengagement of the first and second engaging members to respectively lock and unlock the elongated support member relative to the base member;

wherein the first and second engaging members are spring biased into relative disengagement.

2. The surgical instrument support device of claim 1, wherein the pivot plane is perpendicular to the surface of the surgical support platform.

3. The surgical instrument support device of claim 1, wherein the first engaging member includes a first toothed surface and the second engaging member includes a second toothed surface facing and engageable by the first toothed surface, and wherein the securing mechanism is operative to force into relative engagement or to allow relative disengagement of the first and second toothed surfaces to respectively lock and unlock the support member relative to the base member.

4. The surgical instrument support device of claim 3, wherein angles at which the elongated support member may be locked relative to the base member are selectable based on the number of teeth.

5. The surgical instrument support device of claim 4, wherein the first and second toothed surfaces have a circumferential pattern and the teeth are equally circumferentially spaced apart by a predetermined number of degrees on a common radius of the first and second engaging members.

6. The surgical instrument support device of claim 1, wherein the surgical instrument support device includes a surgical support platform.

7. The surgical instrument support device of claim 1, wherein the extender bar projects from the elongated support member at a nonparallel angle.

8. The surgical instrument support device of claim 1, wherein the extender bar is mounted to the elongated support member for swivelling movement of the extender bar relative to the elongated support member.

9. A surgical instrument support device for positioning a surgical instrument relative to a surface of a surgical support platform, the support device comprising:

a base member fixably mountable to a surgical support platform;

an elongated support member having one end mounted to the base member for pivotal movement of the elongated support member relative to the base member within a pivot plane that is nonparallel to the surface of the surgical support platform;

an extender bar adapted for mounting a surgical instrument with respect thereto, the extender bar being disposed at the other end of the elongated support member, the extender bar projecting from the elongated support member at an angle that is nonparallel to the pivot plane of the elongated support member such that the pivotal movement of the elongated support member raises or lowers the extender bar and the surgical instrument mounted with respect thereto with respect to the surface of the surgical support platform; and a securing mechanism for selectively locking and unlocking the elongated support member relative to the base member to respectively prevent and allow said pivotal movement;

wherein the securing mechanism includes first and second engaging members disposed at the pivot ends of the respective elongated support member and base member, the second engaging member facing and being engageable by the first engaging member, and wherein the securing mechanism is operative to force into relative engagement or to allow relative disengagement of the first and second engaging members to respectively lock and unlock the elongated support member relative to the base member;

wherein the first and second engaging members include respective first and second cavities, and wherein the securing mechanism includes a spring captured at its opposite ends within the cavities for biasing the first and second engaging members into relative disengagement.

10. A surgical instrument support device for positioning a surgical instrument relative to a surface of a surgical support platform, the support device comprising:

a base member fixably mountable to a surgical support platform;

an elongated support member having one end mounted to the base member for pivotal movement of the elongated support member relative to the base member within a pivot plane that is nonparallel to the surface of the surgical support platform;

an extender bar adapted for mounting a surgical instrument with respect thereto, the extender bar being disposed at the other end of the elongated support member, the extender bar protecting from the elongated support member at an angle that is nonparallel to the pivot plane of the elongated support member such that the pivotal movement of the elongated support member raises or lowers the extender bar and the surgical instrument mounted with respect thereto with respect to the surface of the surgical support platform; and a securing mechanism for selectively locking and unlocking the elongated support member relative to the base member to respectively prevent and allow said pivotal movement;

wherein the elongated support member includes a first cam and the base member includes a second cam, and wherein the elongated support member is pivotable over a predetermined angular range limited by the first and second cams contacting one another.

11. The surgical instrument support device of claim 10, wherein the base member includes a coupling adaptor and wherein the surgical instrument support device further includes a vertically extending riser portion and the coupling adaptor connects together the base member and the vertically extending riser portion.

12. The surgical instrument support device of claim 11, wherein the coupling adaptor includes a splined coupling adaptor or a square coupling adaptor.

13. A surgical instrument support device for positioning a surgical instrument extender bar relative to a surface of a surgical support platform, the support device comprising:

an elongated support member fixably mountable with respect to the surface of the surgical support platform and having a pivot plane;

an extender bar mounted to the elongated support member for swivelling movement of the extender bar relative to the elongated support member above the surface of the surgical support platform, the extender bar mounted at an angle that is nonparallel to the pivot plane; and a securing mechanism for selectively locking and unlocking the extender bar relative to the elongated support member to respectively prevent and allow said swivelable movement;

wherein the securing mechanism includes first and second engaging members disposed at the swivel end of the respective extender bar and elongated support member, the second engaging member facing and engageable by the first engaging member, and wherein the securing mechanism is operative to force into relative engagement or to allow relative disengagement of the first and second engaging members to respectively lock and unlock the extender bar relative to the elongated support member;

wherein the first and second engaging members are spring biased into relative disengagement.

14. The surgical instrument support device of claim 13, wherein the first engaging member includes a first toothed surface and the second engaging member includes a second toothed surface facing and engageable by the first toothed surface, and wherein the securing mechanism is operative to force into relative engagement or to allow relative disengagement of the first and second toothed surfaces to respectively lock and unlock the extender bar relative to the elongated support member.

15. The surgical instrument support device of claim 14, wherein angles at which the extender bar may be locked relative to the elongated support member are selectable based on the number of teeth.

16. The surgical instrument support device of claim 15, wherein the first and second toothed surfaces have a circumferential pattern and the teeth are equally circumferentially spaced apart by a predetermined number of degrees on a common radius of the first and second engaging members.

17. The surgical instrument support device of claim 13, wherein the surgical instrument support device includes a surgical support platform.

18. The surgical instrument support device of claim 13, wherein the extender bar projects from the elongated support member at a nonparallel angle.

19. The surgical instrument support device of claim 13, wherein the elongated support member is fixably mountable with respect to the surface of the surgical support platform for pivotal movement of the elongated support member within a pivot plane that is nonparallel to the surface of the surgical support platform.

20. A surgical instrument support device for positioning a surgical instrument extender bar relative to a surface of a surgical support platform, the support device comprising:

an elongated support member fixably mountable with respect to the surface of the surgical support platform and having a pivot plane;

an extender bar mounted to the elongated support member for swivelling movement of the extender bar relative to the elongated support member above the surface of the surgical support platform, the extender bar mounted at an angle that is nonparallel to the pivot plane; and a securing mechanism for selectively locking and unlocking the extender bar relative to the elongated support member to respectively prevent and allow said swivelable movement;

wherein the securing mechanism includes first and second engaging members disposed at the swivel end of the respective extender bar and elongated support member, the second engaging member facing and engageable by the first engaging member, and wherein the securing mechanism is operative to force into relative engagement or to allow relative disengagement of the first and second engaging members to respectively lock and unlock the extender bar relative to the elongated support member;

wherein the first and second engaging members include respective first and second cavities, and wherein the securing mechanism includes a spring captured at its opposite ends within the cavities for biasing the first and second engaging members into relative disengagement.

21. An extension device for a surgical instrument support device having a support bar, the extension device comprising:

a clamp portion;

at least one receptacle disposed in the clamp portion for receiving the support bar from the surgical instrument support device, the clamp portion being positioned to retain the support bar in the receptacle;

an extender bar portion mounted to the clamp portion for pivotal movement of the extender bar portion relative to the damp portion; and a securing mechanism for selectively locking and unlocking the extender bar portion relative to the clamp portion to respectively prevent and allow said pivotal movement;

wherein the at least one receptacle includes first and second receptacles having respective first and second axes defining the direction in which the support bar is received by the respective first and second receptacles, and wherein the first and second axes are disposed at nonparallel angles relative to one another.

22. The extension device of claim 21, wherein the first and second axes are disposed perpendicular to one another.

23. The extension device of claim 21, wherein the extender bar portion pivots relative to the clamp portion about a pivot axis and wherein the first axis is disposed substantially perpendicular to the pivot axis.

24. The extension device of claim 21, wherein the extender bar portion pivots relative to the clamp portion about a pivot axis and wherein the second axis is disposed substantially parallel to the pivot axis.

25. An extension device for a surgical instrument support device having a support bar, the extension device comprising:

a clamp portion;

at least one receptacle disposed in the clamp portion for receiving the support bar from the surgical instrument support device, the clamp portion being positioned to retain the support bar in the receptacle;

an extender bar portion mounted to the clamp portion for pivotal movement of the extender bar portion relative to the clamp portion; and a securing mechanism for selectively locking and unlocking the extender bar portion relative to the clamp portion to respectively prevent and allow said pivotal movement;

wherein the securing mechanism includes first and second engaging members, the second engaging member facing and engageable by the first engaging member, and wherein the securing mechanism is operative to force into relative engagement or to allow relative disengagement of the first and second engaging members to respectively lock and unlock the clamp portion relative to the extender bar portion;

wherein the first and second engaging members are spring biased into relative disengagement.

26. The extension device of claim 25, wherein the securing mechanism includes first and second engaging members, the second engaging member facing and engageable by the first engaging member, and wherein the securing mechanism is operative to force into relative engagement or to allow relative disengagement of the first and second engaging members to respectively lock and unlock the clamp portion relative to the extender bar portion.

27. The extension device of claim 25, wherein the first engaging member includes a first toothed surface and the second engaging member includes a second toothed surface facing and engageable by the first toothed surface, and wherein the securing mechanism is operative to force into relative engagement or to allow relative disengagement of the first and second toothed surfaces to respectively lock and unlock the extender bar portion relative to the clamp portion.

28. The extension device of claim 27, wherein angles at which the extender bar portion may be locked relative to the clamp portion are selectable based on the number of teeth.

29. The extension device of claim 28, wherein the first and second toothed surfaces have a circumferential pattern and the teeth are equally circumferentially spaced apart by a predetermined number of degrees on a common radius of the first and second engaging members.

30. The extension device of claim 25, in combination with a surgical support platform.

31. The extension device of claim 25, wherein the extender bar portion projects from the clamp portion at a nonparallel angle.

32. An extension device for a surgical instrument support device having a support bar, the extension device comprising:

a clamp portion;

at least one receptacle disposed in the clamp portion for receiving the support bar from the surgical instrument support device, the clamp portion being positioned to retain the support bar in the receptacle;

an extender bar portion mounted to the clamp portion for pivotal movement of the extender bar portion relative to the clamp portion; and a securing mechanism for selectively locking and unlocking the extender bar portion relative to the clamp portion to respectively prevent and allow said pivotal movement;

wherein the securing mechanism includes first and second engaging members, the second engaging member facing and engageable by the first engaging member, and wherein the securing mechanism is operative to force into relative engagement or to allow relative disengagement of the first and second engaging members to respectively lock and unlock the camp portion relative to the extender bar portion;

wherein the first and second engaging members include respective first and second cavities, and wherein the securing mechanism includes a spring captured at its opposite ends within the cavities for biasing the first and second engaging members into relative disengagement.

* * * * *